United States Patent [19]

Liu et al.

[11] 4,349,687
[45] Sep. 14, 1982

[54] INTERMEDIATE FOR SYNTHESIS OF THIENAMYCIN VIA (3SR, 4RS)-3-[1 (SR)-HYDROXYETHYL]-2-OXO-4-AZETIDINEACETIC ACID

[75] Inventors: Thomas M. H. Liu, Westfield; David G. Melillo, Scotch Plains; Kenneth M. Ryan, Clark; Ichiro Shinkai, Westfield; Meyer Sletzinger, North Plainfield, all of N.J.

[73] Assignee: Merck & Co., Inc., Rahway, N.J.

[21] Appl. No.: 252,103

[22] Filed: Apr. 8, 1981

Related U.S. Application Data

[63] Continuation of Ser. No. 112,021, Jan. 14, 1980, abandoned.

[51] Int. Cl.³ .................................. C07D 309/30
[52] U.S. Cl. ........................ 549/291; 260/245.2 T; 260/239 A; 560/37; 560/170
[58] Field of Search ..................................... 260/343.5

Primary Examiner—Norma S. Milestone
Attorney, Agent, or Firm—Frank M. Mahon; James A. Arno; Hesna J. Pfeiffer

[57] ABSTRACT

Disclosed is a process for the stereocontrolled total synthesis of thienamycin via intermediates II and IIa:

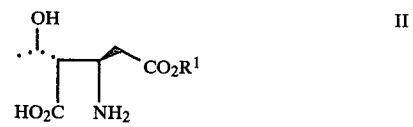

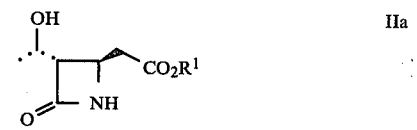

wherein R is a readily removable carboxyl protecting group.

1 Claim, No Drawings

INTERMEDIATE FOR SYNTHESIS OF THIENAMYCIN VIA (3SR, 4RS)-3-[1 (SR)-HYDROXYETHYL]-2-OXO-4-AZETIDINEACETIC ACID

This is a continuation of application Ser. No. 112,021, filed Jan. 14, 1980, now abandoned.

BACKGROUND OF THE INVENTION

This invention relates to a stereocontrolled total synthesis of the known antibiotic thienamycin (I).

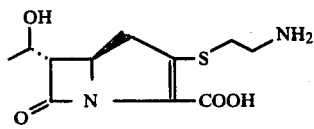
I

Starting from acetone dicarboxylate, the synthesis proceeds in a stereo-selective way via intermediates II and IIa.

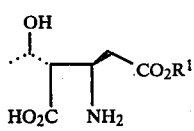
II

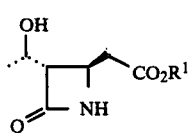
IIa wherein $R^1$ is a readily removable protecting group such as benzyl, $\beta,\beta,\beta$-trichloroethyl, methyl, ethyl, phenyl, t-butyl and the like.

DETAILED DESCRIPTION OF THE INVENTION

The process of the present invention may conveniently be summarized by the following reaction diagram:

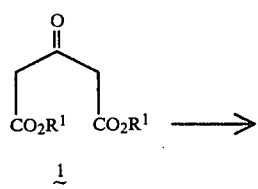
1

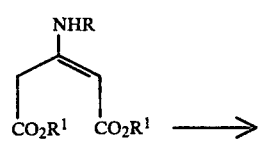
2

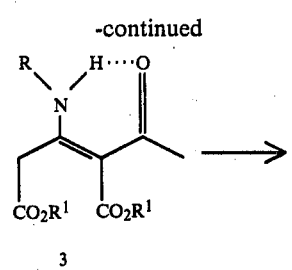
3

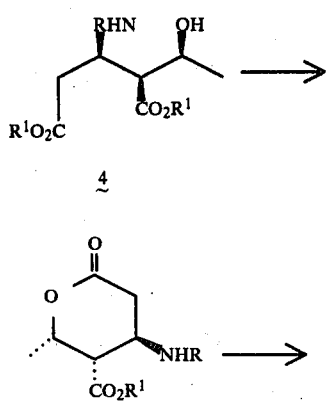
4

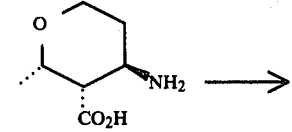
5

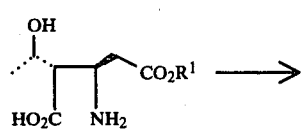
5a

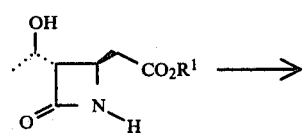
5b

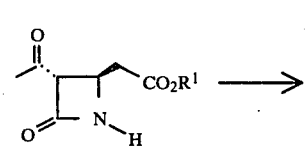
5c

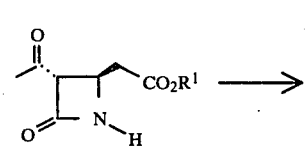
5d

-continued

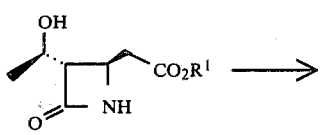

6

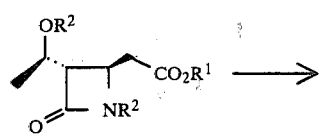

7

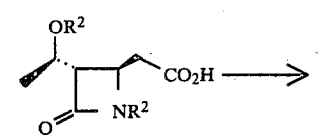

8

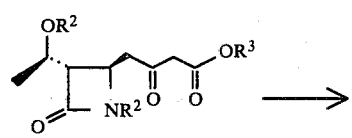

9

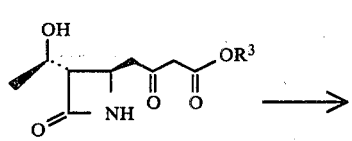

10

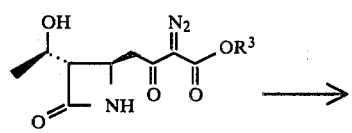

11

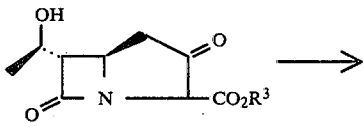

12

-continued

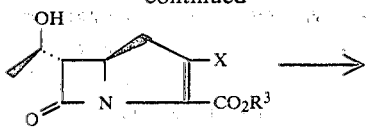

13

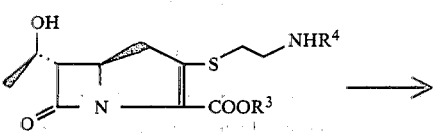

14

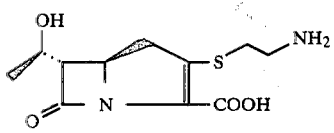

I

In words relative to the above reaction diagram, the acetone dicarboxylate starting material 1 ($R^1$ is alkyl having from 1-6 carbon atoms, aryl, such as phenyl, or aralkyl having from 7-12 carbon atoms) in a solvent such as toluene, methylene chloride, ethyl acetate, ether or the like is treated with an amine, $NH_2R$ (R is hydrogen; phenylalkyl having from 7-12 carbon atoms such as benzyl; 2,4-dimethoxybenzyl; alkyl having from 1-6 carbon atoms such as t-butyl; or an amine, such as α-methylbenzylamine, or the like) at a temperature of from −10° to 110° C., for from 0.5 to 24 hours. The above reaction mixture for the transformation 1→2 is conducted in the presence of a dehydrating agent such as sodium sulfate, molecular sieves, or the like.

The transformation 2→3 is accomplished by treating 2 in a solvent such as toluene, methylene chloride, ethyl acetate, ether or the like with a stoichiometric to 100-fold excess of ketene, acetic anhydride, or acetyl halide such as acetyl chloride in the presence of a base such as a triorganoamine, for example, triethylamine, at a temperature of from −10° to 95° C. for from 10 minutes to 15 hours.

The transformation 3→4 is accomplished by treating 3 in a solvent such as acetic acid, ethanol, methanol or the like at a temperature of from 0° to 80° C. with a reducing agent such as sodium cyanoborohydride, sodium borohydride, sodium acetoxyborohydride, or the like, in the presence of a carboxylic acid such as acetic, tartaric, oxalic or the like.

Cyclization of 4 to form the lactone 5 is accomplished by treating 4 in a solvent such as methylene chloride, ether, toluene, water, or the like with an acid such as hydrochloric, sulfuric, phosphoric, trifluoroacetic, or the like at a temperature of from 0° to 100° for from 0.5 to 20 hours. Cyclization of 4 to form 5, wherein $R^1$ is hydrogen, is accomplished by heating a solution of 4 in concentrated aqueous HCl or equivalent acid, at from 25° to 100° C. for from 2 to 12 hours. It should be noted that these latter conditions will also convert 5 ($R^1$=protecting group) to 5 ($R^1$=hydrogen).

The deblocking transformation 5→5a is typically achieved by catalytic hydrogenation in a solvent such as acetic acid, water, or the like under a hydrogenation pressure of from 40–1500 psi in the presence of a hydrogenation catalyst such as palladium on charcoal, palladium hydroxide, platinum oxide or the like.

The transformation 5a→5b is accomplished by treating 5a with an alcohol such as benzyl alcohol, 2,2,2-trichloroethanol, methanol, phenol or the like at a temperature of from 25°–100° C. for from 1 to 24 hours. The value of $R^1$ is determined by the alcohol $R^1OH$ utilized in the transformation 5a→5b. Suitable values for $R^1$ have generically been defined above relative to starting material 1.

It should be noted that intermediate 5a is racemic. Resolution at this stage to the desired 2S,3S,4R-isomer affords optically pure thienamycin on completion of the synthesis. Resolution of 5a (or its protected intermediate 5) is conveniently accomplished by crystallization with an optically active acid. The preferred means of resolution is accomplished on crystallization with camphorsulfonic acid, (−) or (+) phenethylsulfonic acid and (−) or (+) α-methoxy-α-trifluoromethylphenylacetic acid, or the like. Such resolution is described and claimed in concurrently filed, commonly assigned U.S. patent application Ser. No. 112,020, filed Jan. 14, 1980, now abandoned in favor of U.S. patent application Ser. No. 291,523, filed Aug. 10, 1981 [Merck and Co., Inc., George Gal, et al.]; this application is incorporated herein by reference to the extent that it describes the resolution of 5a.

The transformation 5b→5c is accomplished by treating 5b with dicyclohexylcarbodiimide (DCC), or the like in the presence of a base such as triethylamine, 4-dimethylaminopyridine, pyridine, or the like.

The oxidation 5c→5d is accomplished with an oxidizing agent such as Jones reagent, dipyridine chromium (VI)·oxide, trifluoroacetic anhydride-dimethylsulfoxide-triethylamine, pyridinium dichromate, acetic anhydride-dimethylsulfoxide-triethylamine in a solvent such as methylene chloride, acetonitrile, or the like at a temperature of from −78° to 25° C. for from 5 minutes to 5 hours.

The reduction 5d→6 is accomplished by treating the ketone with a reducing agent such as sodium cyanoborohydride, potassium tri(sec-butyl)borohydride, lithium tri(sec-butyl)borohydride, sodium borohydride, lithium aluminum hydride or the like in a solvent such as diethylether, tetrahydrofuran, toluene or the like at a temperature of from −20° to 25° C. The reaction can conveniently be conducted in the presence of an added complexing salt such as potassium iodide, magnesium bromide or the like.

Establishment of protecting group $R^2$ is accomplished by the transformation 6→7. Preferably 6 in a solvent such a dimethylformamide, ethyl acetate, methylene chloride, or the like is reacted with a reagent capable of establishing $R^2$. Preferred protecting groups are triorganosilyls such as tert-butyldimethylsilyl, or the like. Typically, protecting groups $R^2$ are established by treating 6 in a solvent such as dimethylformamide, ethylacetate, methylene chloride, or the like in the presence of a base such as pyridine, triethylamine, or the like with a stoichiometric to 4-fold excess of tert-butyldimethylsilyl chloride at a temperature of from 25° to 70° C. for from 3 to 48 hours.

It should be noted that establishment of protecting group $R^2$ is optional; the chain elongation reaction 8→9 can efficiently be accomplished when $R^2$=hydrogen.

The deblocking of the carboxyl group is accomplished in the transformation 7→8. Typically the deprotection is accomplished by catalytic hydrogenation. Typically, 7 and the solvent such as methanol, ethylacetate, ether, or the like under a hydrogen pressure of from 1 to 3 atmospheres in the presence of a hydrogenation catalyst such as palladium on charcoal, platinum oxide, or the like is held at a temperature of from 0° to 40° C. for from 1 to 3 hours, to provide 8. Other deblocking procedures, such as hydrolysis, are also appropriate. Thus, for example, when $R^1$ is methyl, basic hydrolysis is preferred: Typically, this is accomplished by the addition of an equivalent amount of a base such as NaOH, KOH, Ba(OH)$_2$, Na$_2$CO$_3$, or the like to an aqueous solution of 7 (for example, as the methyl ester) at 25°–100° C. for from 1.0 min. to 10 hours.

The addition 8→9 is accomplished by treating 8 with 1,1′-carbonyldiimidazole or the like in a solvent such as tetrahydrofuran, dimethoxyethane, or the like at a temperature of from 0° to 50° C., followed by the addition of 1.1 to 3.0 equivalents of $(R^3O_2CCH_2CO_2)_2Mg$, or the like at a temperature of from 0° to 50° C. for from 1 to 48 hours. $R^3$ is a readily removable carboxyl protecting group such as p-nitrobenzyl, o-nitrobenzyl, benzyl or the like.

The removal of the protecting groups $R^2$ is accomplished by treating 9 in a solvent such as 10% aqueous methanol, tetrahydrofuran, or the like in the presence of hydrochloric acid, sulfuric acid, phosphoric acid, or the like at a temperature of 0° to 50° C. for from 10 minutes to 10 hours to provide intermediate 10.

The diazotization reaction 10→11 is accomplished by treating 10 in a solvent such as ethyl acetate, methylene chloride, toluene, or the like, with a diazotization reagent such as p-toluenesulfonyl azide, p-carboxybenzenesulfonyl azide or the like in the presence of a base such as pyridine, triethylamine, or the like at a temperature of from 0° to 40° C. for from 10 to 120 minutes.

Cyclization (11→12) is accomplished by treating 11 in a solvent such as benzene, toluene, THF or the like at a temperature of from 50°–110° C. for from 1–5 hours in the presence of a catalyst such as bis(acetylacetonato) Cu (II) [Cu(acac)$_2$], CuSO$_4$, Cu powder, Rh$_2$(OAc)$_4$, or Pd(OAc)$_2$. Alternatively, the cyclization may be accomplished by irradiating 11 through a pyrex filter (a wave length greater than 300 nm) in a solvent such as benzene, CCl$_4$, diethylether or the like at a temperature of from 0°–25° C. for from 0.5 to 2 hours. ["OAc"=acetate].

Establishment of leaving group X (12→13) is accomplished by reacting the keto ester 12 with R°X such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, or the like; wherein: X is the corresponding leaving group such as toluene sulfonyloxy, p-nitrophenylsulfonyloxy, methanesulfonyloxy, p-bromophenylsulfonyloxy; or other leaving groups which are established by conventional procedures and are well known in the art. Typically, the above reaction to establish leaving groups X is conducted in a solvent such as methylene chloride, acetonitrile or dimethylformamide, in the presence of a base such as diisopropylethylamine, triethylamine, 4-dimethylaminopyridine or the like at a temperature of from −20° to 40° C. for from 0.5 to 5 hours. The leaving group X of intermediate 13 can also be halogen. The halogen leaving group is established by treating 12 with a halogenating agent such as φ₃PCl₂, φ₃PBr₂, (φO)₃PBr₂, oxalyl chloride or the like in a solvent such as CH₂Cl₂, CH₃CN, THF, or the like in the presence of a base such as diisopropylethylamine, triethylamine, or 4-dimethylaminopyridine or the like. [φ=phenyl.]

The leaving group X can also be a phosphate. It is typically prepared by treating 12 with diethyl chlorophosphate or the like in the presence of a base such as diisopropylethylamine, triethylamine, or 4-dimethylaminopyridine or the like.

The leaving group X can also be a carbonate. It is prepared by treating 12 with a chloroformate such as methyl, benzyl, p-nitrobenzyl or the like in the presence of a base such as diisopropylethylamine, triethylamine, or 4-dimethylaminopyridine or the like.

The leaving group X can also be an imino ester:

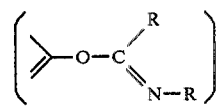

It is prepared by treating 12 with an imidoyl chloride such as N-phenyl trimethylacetimido chloride in the presence of a base such as diisopropylethylamine, triethylamine, or 4-dimethylaminopyridine or the like.

The reaction 13→14 is accomplished by treating 13 in a solvent such as dioxane, dimethylformamide, dimethylsulfoxide, acetonitrile, hexamethylphosphoramide, or the like in the presence of an approximately equivalent to excess of the mercaptan reagent HSCH₂CH₂NHR⁴ wherein R⁴ is hydrogen or a readily removable N-protecting group such as p-nitrobenzyloxycarbonyl, o-nitrobenzyloxycarbonyl, formimidoyl, phenoxyacetyl, phenylacetyl, 2-methyl-2-(o-nitrophenoxy)propionic, and o-nitrophenoxyacetic, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, HSCH₂CH₂NHR⁴, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step 14→I is accomplished by conventional procedures such as hydrolysis or hydrogenation, or enzymatically. Typically 14 in a solvent such as dioxane-water-ethanol; tetrahydrofuran-aqueous dipotassium hydrogen phosphate-isopropanol; tetrahydrofuran-water-morpholinopropane-sulfonic acid (adjusted pH to 7.0 by adding sodium hydroxide); or the like is treated under a hydrogen pressure of from 1 to 4 atmospheres in the presence of a hydrogenation catalyst such as palladium on charcoal, palladium hydroxide, platinum oxide, or the like at a temperature of from 0° to 50° C. for from 0.5 to 4 hours to provide I.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. All temperatures are in °C.

EXAMPLE 1

3-Benzylamino-2-pentenedioic acid diethyl ester (2)

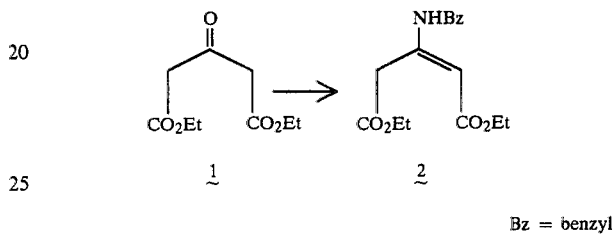

Bz = benzyl

Benzylamine (89.1 g, 0.83 moles) is added over 10 minutes to a suspension of 5 A powdered molecular sieves (270 g) and diethyl 1,3-acetonedicarboxylate (160 g) (0.79 moles) in 350 ml toluene (external cooling applied to control exotherm). The suspension is stirred at room temperature for 14–17 hours and then filtered to provide 2. The filter cake is washed with three portions of toluene. The combined filtrates may be used as is in the subsequent ketene reaction.

EXAMPLE 2

2-Acetyl-3-benzylamino-2-pentenedioic acid diethyl ester (3)

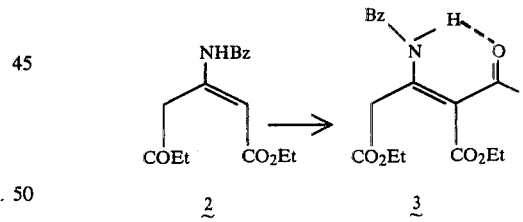

Ketene gas (generated by pyrolysis of acetone) is passed through the stirred solution of 2 (see Example 1, above) at 22° C. When starting material 2 is completely consumed (followed by TLC—solvent system 1:1 hexane/EtOAc), the solution is concentrated to give the product as a tan solid.

Yield=270.2 g (103%, purity by NMR ca 90%).

Recrystallization from ethanol affords the pure product 3 as colorless needles, mp 87°-8° C.

| Elem. anal. | | Calc. | Found |
|---|---|---|---|
| C₁₈H₂₃NO₅ | C | 64.85% | 64.90% |
| | H | 6.95 | 7.06 |
| | N | 4.20 | 3.94 |

EXAMPLE 3

(2SR, 3RS)-2-[1(SR)-hydroxyethyl]-3-(benzylamino)pentanedioic acid diethyl ester 4

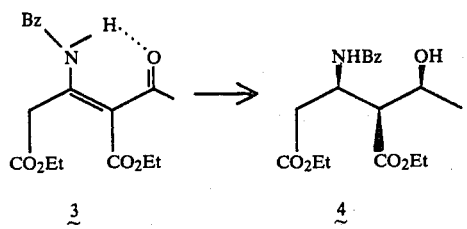

A solution of the enamine 3 (83.3 g, 0.25 mmoles) in 400 ml HOAc (acetic acid) is chilled to ca. 10° C. and sodium cyanoborohydride (20.9 g, 0.33 moles) is added as a solid portionwise over 15–30 minutes. The cooling bath is removed and the solution stirred at room temperature (22° C.) for 3.5 hours. The solution is concentrated in vacuo and the residue flushed with toluene to remove most of the acetic acid. The residue is partitioned between 400 ml EtOAc (ethyl acetate) and 300 ml saturated aqueous NaHCO$_3$. The organic layer is washed with another 300 ml portion of aqueous NaHCO$_3$. The combined aqueous layers are back extracted with 200 ml EtOAc. The organic layers are dried (Na$_2$SO$_4$) and concentrated in vacuo to give 4 as a colorless gum, 100 g.

EXAMPLE 4

Tetrahydro-2α-methyl-6-oxo-4β-benzylamino-2H-pyran-3α-carboxylic acid hydrochloride 5

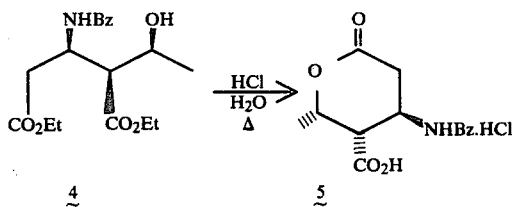

The crude amino alcohol 4 (110 g) is cautiously dissolved in 900 ml concentrated aqueous HCl. The solution is heated to reflux and 80–100 ml of distillate is collected (discarded) during the first hour of reflux. After a 3 hr. reflux period the solution is cooled to 0° for 45 min and filtered. The solid is washed with three portions of 40% EtOH in isopropanol and dried in vacuo to constant weight to yield 5: 24–30 g of white crystalline solid; mp 160°–170° (dec).

| Elem. Anal. | | Calcd. | Found |
|---|---|---|---|
| C$_{14}$H$_{18}$ClNO$_4$.H$_2$O | C | 52.91 | 52.79 |
| | H | 6.34 | 6.41 |
| | Cl | 11.16 | 11.00 |
| | N | 4.41 | 4.51 |

EXAMPLE 4a

Tetrahydro-2α-methyl-6-oxo-4β-benzylamino-2H-pyran-3α-carboxylic acid ethyl ester hydrochloride 5

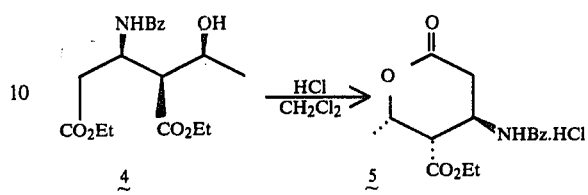

A similar batch of crude amino alcohol 4 (101.7 g) in 900 ml CH$_2$Cl$_2$ is treated with HCl gas (subsurface introduction) for 1 hour. The saturated solution (or suspension) is stirred at room temperature for another 2 hours. Ether (800 ml) is added to the suspension and cooled to 0° for 1 hr. The solid is collected, washed with two cold portions of CH$_2$Cl$_2$ and dried in vacuo to yield 5:

Yield: 26.6 g (35% from diethyl 1,3-acetonedicarboxylate) mp 181°–7° (dec).

| Elem. Anal. | | Calcd | Found |
|---|---|---|---|
| C$_{16}$H$_{22}$ClNO$_4$ | C | 58.62 | 58.95 |
| | H | 6.77 | 6.79 |
| | Cl | 10.82 | 10.94 |
| | N | 4.27 | 4.69 |

EXAMPLE 5

(3SR, 4RS)-1-(tert-butyldimethylsilyl)-3-[1(RS)-tert-butyldimethylsilyloxyethyl]-2-oxo-4-azetidineacetic acid benzyl ester 11

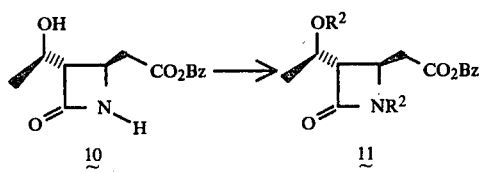

R$^2$ = —Si[C(CH$_3$)$_3$](CH$_3$)$_2$

Triethylamine (0.937 g, 9.28 mmole) in 3 ml DMF (sieve-dried) is added to the β-lactam (1.056 g, 4.01 mmol) in 15 ml DMF at room temperature. The solution is chilled to 0° and tert-butyldimethylsilyl chloride (1.39 g, 9.28 mmole) is added as a solid in 3 portions over 5 minutes. The suspension is aged at 0° for 15 minutes then at room temperature for 19 hours. The orange-brown suspension is diluted with H$_2$O and extracted with EtOAc. The organic layer is washed with H$_2$O, brine, dried and concentrated to give the product 11 as a colorless gum (2.0 g) that solidifies on standing.

EXAMPLE 6

(3SR, 4RS)-1-(tert-butyldimethylsilyl)-3-[1(RS)-tert-butyl-dimethylsilyloxyethyl]-2-oxo-4-azetidineacetic acid 12

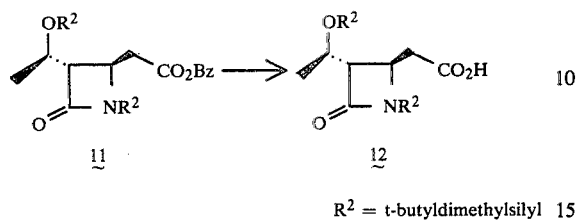

R² = t-butyldimethylsilyl

A suspension of the crude benzyl ester 11 (2.00 g, 4.01 mmole) and ½ g 10% Pd/C in 40 ml. MeOH is pressurized (40 psi) with H₂ and shaken for 75 minutes. The suspension is filtered and the filtrate is concentrated in vacuo to give the product 12 as a white solid, 1.60 g.

Analytical sample from EtOAc as white needles, m.p. 168°-9°

| Calcd. for | | Calculated | Found |
|---|---|---|---|
| C₁₉H₃₉NO₄Si₂ | C | 56.81 | 56.95 |
| | H | 9.79 | 9.98 |
| | N | 3.49 | 3.45 |
| | Si | 13.98 | did not analyze properly |

EXAMPLE 7

(3SR, 4RS)-1-(tert-butyldimethylsilyl)-3-[1(RS)-tert-butyl-dimethylsilyloxyethyl]-β,2-dioxo-4-azetidinebutanoic acid p-nitrobenzyl ester 13

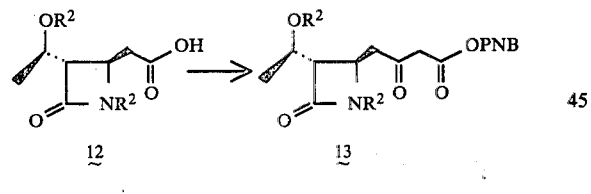

PNB = p-nitrobenzyl
R² = t-butyldimethylsilyl

To a solution of the β-lactam 12 (1.46 g., 3.62 mmole) in 30 ml. CH₂Cl₂ at room temperature is added 1,1'-carbonyldiimidazole (0.64 g., 3.95 mmole). After stirring for 30 minutes the solution is treated with 2,2-dimethyl-1,3-dioxane-4,6-dione (0.78 g., 5.43 mmole) and 4-dimethylaminopyridine (0.66 g., 5.43 mmole) and the solution aged at room temperature for another 70 hours. The solution is washed with 1 N aqueous HCl followed by H₂O and then dried with Na₂SO₄ and concentrated. The residue is dissolved in 20 ml. MeCN, p-nitrobenzyl alcohol (0.94 g., 6.15 mmole) is added, and the solution is heated to reflux for 1 hour. The reaction mixture is concentrated to a gummy solid. The pure product 13 is isolated by crystallization from isopropanol; or by chromatography on silica gel (eluent, hexane-EtOAc, 7/3).

Analytical sample from 1/1 hexane/Et₂O, colorless needles, m.p. 113.5°-115°.

| Calcd. for | | Calcd. | Found |
|---|---|---|---|
| C₂₈H₄₆N₂O₇Si₂ | C | 58.09 | 58.31 |
| | H | 8.01 | 8.25 |
| | N | 4.84 | 4.76 |
| | Si | 9.70 | did not analyze properly |

EXAMPLE 8

(3SR, 4RS)-3-(1(RS)-hydroxyethyl)-β,2-dioxo-4-azetidinebutanoic acid p-nitrobenzyl ester

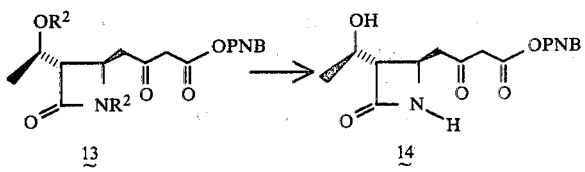

PNB = p-nitrobenzyl
R² = t-butyldimethylsilyl

Concentrated aqueous HCl (0.45 ml) is added to a suspension of the silyl derivative (0.63 g., 1.09 mmole) in 30 ml. of 10% aqueous MeOH. After stirring at room temperature for 6 hours, the solution is concentrated almost to dryness. The residue containing 14 is partitioned between H₂O and CH₂Cl₂. The organic layer is dried MgSO₄) and concentrated to a colorless gum, 0.40 g. The crude product is used as is in the next step.

Analytical sample from hexane/EtOAc, m.p. 97°-9°.

| Calcd. for | | Calcd. | Found |
|---|---|---|---|
| C₁₆H₁₈N₂O₇ | C | 54.85 | 55.02 |
| | H | 5.18 | 5.38 |
| | N | 8.00 | 7.79 |

EXAMPLE 9

(3SR, 4RS)-α-diazo-3-[1(RS)-hydroxyethyl]-β,2-dioxo-4-azetidinebutanoic acid p-nitrobenzyl ester 15

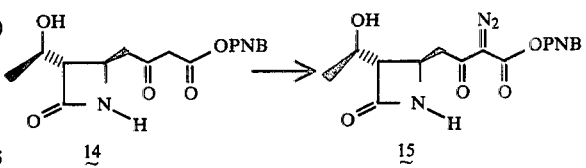

A solution of the crude β-keto ester 14 (0.83 g., 2.37 mmole) and p-toluenesulfonyl azide (0.56 g, 2.85 mmole) in 10 ml EtOAc at room temperature is treated with a solution of NEt₃ (0.31 g., 3.08 mmole) in 2 ml. EtOAc. The resulting suspension is stirred for 1 hr., chilled to 0° and filtered. The product 15 (0.77 g) is analytically pure, m.p. 160.5°-2° (dec.).

| Elem. Anal. | | Calcd. | Found |
|---|---|---|---|
| C₁₆H₁₆N₄O₇ | C | 51.06 | 51.04 |
| | H | 4.29 | 4.22 |

| Elem. Anal. | Calcd. | Found |
|---|---|---|
| N | 14.89 | 14.76 |

EXAMPLE 10

(5RS,6SR)-6-[(RS)-1-hydroxyethyl]-3,7-dioxo-1-azabicyclo[3.2.0]heptane-2-carboxylic acid p-nitrobenzyl ester

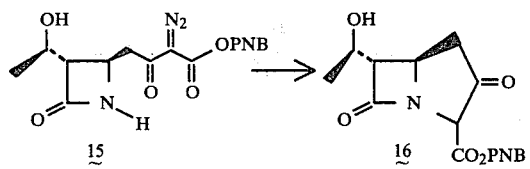

A stirred suspension of the diazo compound 15 (500 mg, 1.33 mmole) and rhodium diacetate (15 mg) in dry toluene (35 ml) is heated to 80°-5° for 2.5 hours. After filtration of the catalyst, the solution is concentrated in vacuo to give the product as a white solid, mp 92°-8°.

EXAMPLE 11

(5RS,6SR)-6-[(RS)-1-hydroxyethyl]-3-[2-(p-nitrobenzyloxycarbonyl)aminoethylthio]-7-oxo-1-azabicyclo[3.2.0]hept-2-ene-2-carboxylic acid p-nitrobenzyl ester

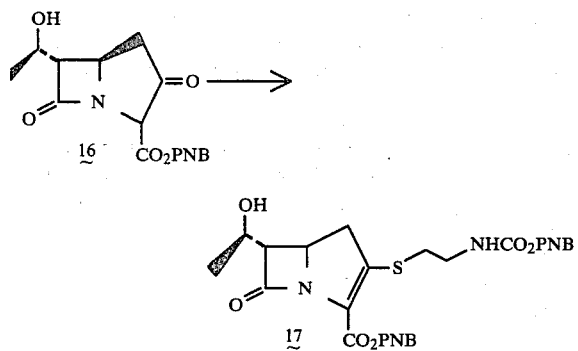

PROCEDURE A: Trifluoromethylsulfonyl Activation

To a stirred suspension of the bicyclic ketone 16 (100 mg, 0.287 mmole) in dry methylene chloride (1 ml) is added dropwise a solution of diisopropylethylamine (62 mg, 0.481 mmole) in dry $CH_2Cl_2$ (0.4 ml) at 0° C. under a nitrogen atmosphere. The resulting mixture is aged for 15 min. then trifluoromethanesulfonic anhydride (90 mg, 0.319 mmole) is added to give a clear solution. To the mixture is added a solution of diisopropylethylamine (250 mg, 1.94 mmole) in $CH_2Cl_2$ (0.3 ml) followed by N-p-nitrobenzyloxycarbonylcysteamine (77 mg, 0.30 mmole) as a solid at 0° C. The mixture is stirred for 30 min during which time the product crystallizes as a colorless solid. The solid is collected by filtration and washed with $CH_2Cl_2$. An additional crop of product is obtained by washing the filtrate with dilute aqueous $NaHCO_3$. The organic layer is dried with $Na_2SO_4$ and concentrated in vacuo. The residue is crystallized from EtOAC. The combined yield is 108 mg (64%) of product 17.

PROCEDURE B: Tosylate Activation

To a suspension of the bicyclic ketone 16 (50 mg, 0.144 mmole) in acetonitrile (3 ml) is added dropwise a solution of diisopropylethylamine (22 mg, 0.171 mmole) in 1 ml $CH_3CN$ at $-5°$ C. under a nitrogen atmosphere. After aging at this temperature for 10 min, a solution of p-toluene sulfonic anhydride (51 mg, 0.156 mmole) in 1 ml $CH_3CN$ is added. The resulting mixture is stirred for 2 hr. at 0° C. The solution is concentrated in vacuo to a volume of approximately 1 ml and then 3 ml of dry N,N-dimethylformamide (DMF) is added and the remaining $CH_3CN$ removed in vacuo. To the DMF solution at $-5°$ C. is added a solution of diisopropylethylamine (40 mg, 0.31 mmole) in 0.5 ml DMF and the resulting mixture stored in a refrigerator for 70 hrs. The solution is diluted with brine and extracted with five portions of $CH_2Cl_2$. The combined extracts are washed with brine, dried over $Na_4SO_4$, and concentrated in vacuo. The residue is crystallized from an ethylacetate-ether mixture to give the product 17 as a colorless solid, 68 mg (81%).

PROCEDURE C: Phosphate activation

To a suspension of the bicyclic ketone 16 (100 mg, 0.29 mmole) in $CH_3CN$ (1 ml) is added dropwise a solution of diisopropylethylamine (37 mg, 0.29 mmole) in 0.4 ml $CH_3CN$ at 0° under a nitrogen atmosphere. The resulting mixture is stirred for 15 min then a solution of diphenyl chlorophosphate (77 mg, 0.29 mmole) in 0.4 ml $CH_3CN$ is added. The mixture is stirred for 15 min at 0° and then 15 min at room temperature. The mixture is again cooled to 0° and a solution of diisopropylethylamine (38.7 mg, 0.30 mmole) in 0.4 ml $CH_3CN$ is added followed by N-p-nitrobenzyloxycarbonylcysteamine (77 mg, 0.30 mmole). The reaction mixture is stored overnight in a freezer, diluted with EtOAC, and filtered to give the product 17 as a colorless solid, 118 mg (70%).

EXAMPLE 12

Thienamycin

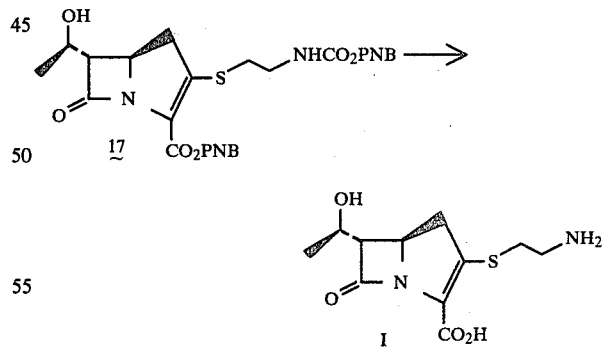

A mixture of the protected thienamycin 17 (4.9 mg, $8.362 \times 10^{-6}$ mole) and platinum oxide (3.4 mg) in tetrahydrofuran (2 ml), water (1 ml) and 0.5 M morpholinopropane sulfonic acid (adjusted to pH 7.0 by adding sodium hydroxide) (0.5 ml) is hydrogenated at 40 psi on a Parr shaker for 60 minutes. The suspension is filtered to remove catalyst and the catalyst is washed with water (2×20 ml). The filtrate is washed with EtOAC (2×15 ml). The aqueous layer is diluted to 50 ml and assayed for thienamycin.

UV $\lambda_{max}$=298 mm

HPLC assay 84.1% yield, retention time=298 sec., natural thienamycin 298 sec.

EXAMPLE 13

Tetrahydro-2α-methyl-6-oxo-4β-amino-2H-pyran-3α-carboxylic acid hydrochloride

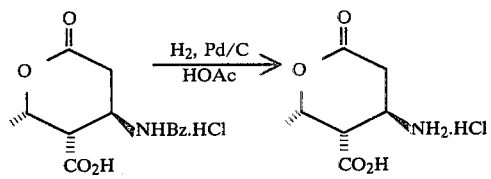

A suspension of the benzyl lactone (5.00 g 0.0167 moles) and 1.0 g of 10% Pd/C in 200 ml acetic acid is pressurized to 1500 psi with hydrogen. The mixture is agitated at room temperature for 3 days, vented, and filtered. The recovered catalyst is washed with 2 portions (ca. 15 ml) of HOAc. The combined filtrates are concentrated in vacuo.

Yield=4.00 g (114%) of white, foamy gum containing residual acetic acid.

Analytical sample prepared by crystallization from an acetic acid-acetonitrile-toluene mixture, mp 160°-5° (dec).

| Elem. Anal. | | Calcd. | Found |
|---|---|---|---|
| $C_7H_{12}ClNO_4$ | C | 40.10 | 40.05 |
| | H | 5.77 | 5.90 |
| | N | 6.68 | 6.93 |
| | Cl | 16.91 | 16.97 |

EXAMPLE 14

(2SR, 3RS)-3-amino-2[1(SR)-hydroxyethyl]pentanedioic acid 5-benzyl ester hydrochloride

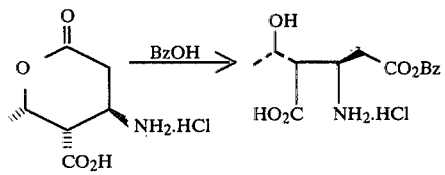

The crude amino acid (2.90 g, ca. 12.1 mmole) is dissolved in 40 ml. of benzyl alcohol and heated to 70°-75° for 1 day. The solution is diluted with toluene (70 ml) and the product extracted with 2 portions (20 ml each) H₂O. The combined aqueous layers are washed with toluene (40 ml) and concentrated in vacuo, to give 3.10 g of crude product as a foamy gum.

This crude material can be used as is for the next step. Alternatively, pure, crystalline material can be obtained as follows:

Acetonitrile (40 ml) is added to 2.61 g of the crude amino acid and the mixture is stirred until the gum is all transformed to white solid (1-2 hrs.). The suspension is cooled to 0°, filtered, and washed with isopropyl alcohol.

Yield=1.90 g white powder (59% yield from benzyl lactone).

| Elem. Anal. | | Calcd. | Found |
|---|---|---|---|
| $C_{14}H_{20}ClNO_5$ | C | 52.91 | 52.80 |
| | H | 6.34 | 6.54 |
| | Cl | 11.16 | 11.00 |
| | N | 4.41 | 4.33 |

The combined filtrates containing additional product and unreacted lactone can be concentrated and recycled.

EXAMPLE 15

(3SR, 4RS)-3-[1(SR)-hydroxyethyl]-2-oxo-4-azetidineacetic acid benzyl ester

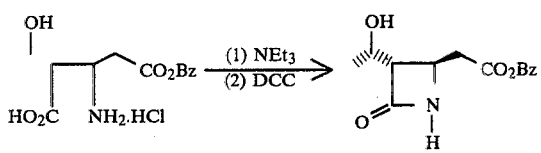

Triethylamine (5.24 g, 51.9 mmol) is added to a suspension of the pure amino acid (16.00 g, 50.3 mmol) in 200 ml acetonitrile at room temperature. The mixture is aged for 5 minutes, then N,N'-dicyclohexylcarbodiimide (10.88 g, 52.8 mmol) is added as a solid. After aging at room temperature for 10 minutes, the suspension is heated to 60° for 3 hours and then concentrated. The residue is slurried in cold EtOAc and filtered to remove the urea. The filtrate is washed successively with 2 N HCl, H₂O, satd. NaHCO₃ (these extracts are all back-extracted with EtOAc), and brine, dried (MgSO₄) and concentrated. The crude product (13.2 g) is pure enough (the only impurity is about 5% of the cyclohexylurea) to use in the subsequent steps, however, analytically pure material may be prepared either by crystallization from diethyl ether or chromatography on silica gel (eluent, 20% hexane-EtOAc), mp 67.5°-68.5°.

| Elem. Anal | Calcd | Found |
|---|---|---|
| C | 63.86 | 63.86 |
| H | 6.51 | 6.56 |
| N | 5.32 | 5.43 |

EXAMPLE 16

(3SR, 4RS)-3-acetyl-2-oxo-4-azetidineacetic acid benzyl ester

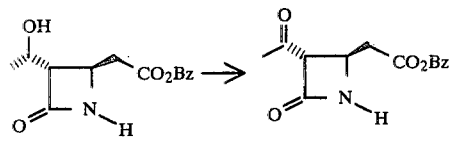

The alcohol (1.07 g, 4.07 mmole) in 20 ml acetone is cooled to 0° and treated with Jones reagent (prepared according to Eisenbraun, *Organic Syntheses,* Coll. Vol. V, pg 310) until the orange color of the reagent persists. The mixture is aged 15 min. and the excess reagent destroyed by addition of 0.2 ml isopropanol. The mixture is concentrated and the residue partitioned between EtOAc and dilute aqueous HCl. The organic layer is washed with brine, dried with Na₂SO₄ and concentrated to give the product as a pale yellow solid (0.96 g).

EXAMPLE 17

(3SR,4RS)-3-[1(RS)-hydroxyethyl]-2-oxo-4-azetidineacetic acid and (3SR,4RS)-3-[1(SR)-hydroxyethyl]-2-oxo-4-azetidineacetic acid benzyl ester

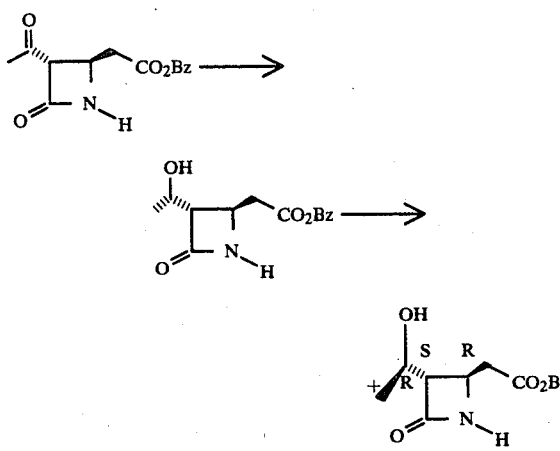

To a solution of the ketone (249 mg, 0.95 mmole) in 3 ml HOAc at room temperature is added sodium cyanoborohydride (60 mg, 0.95 mmole) as a solid. The solution is aged for 1 hour and concentrated in vacuo. The residue is partitioned between EtOAc and saturated aqueous NaHCO₃ (2 portions). The organic layer is dried (Na₂SO₄) and concentrated to a gum. The crude product containing both isomeric alcohols is crystallized from EtOAc/hexane to give the RSR/SRS alcohol as colorless needles.

The mother liquor can be re-oxidized and recycled.

CROSS REFERENCE TO RELATED APPLICATIONS

The following concurrently filed, commonly assigned U.S. patent applications are similarly directed to totally synthetic schemes for the preparation of thienamycin and in that respect complement the disclosure of the present application; consequently, these applications are incorporated herein by reference.

1. U.S. patent application Ser. No. 112,058 filed Jan. 14, 1980, now abandoned in favor of U.S. patent application Ser. No. 255,193, filed Apr. 17, 1981 [Merck and Co., Inc., Thomas M. H. Liu, et al.]

2. U.S. patent application Ser. No. 112,020 filed Jan. 14, 1980, now abandoned in favor of U.S. patent application Ser. No. 291,523, filed Aug. 10, 1981 [Merck and Co., Inc., George Gal, et al.]

3. U.S. patent application Ser. No. 112,021 filed Jan. 14, 1980, now abandoned in favor of U.S. patent application Ser. No. 252,103, filed Apr. 8, 1981 [Merck and Co., Inc., Thomas M. H. Liu, et al.]

4. U.S. patent application Ser. No. 112,057 filed Jan. 14, 1980, now U.S. Pat. No. 4,269,772, issued May 26, 1981 [Merck and Co., Inc., David G. Melillo, et al.]

5. U.S. patent application Ser. No. 112,022 filed Jan. 14, 1980 [Merck and Co., Inc., Thomas M. H. Liu, et al.]

What is claimed is:

1. The compound having the structural formula:

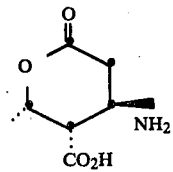

* * * * *